(12) United States Patent
Ilic et al.

(10) Patent No.: US 6,428,665 B1
(45) Date of Patent: Aug. 6, 2002

(54) ELECTROCHEMICAL GAS SENSOR

(75) Inventors: Dejan Ilic, Ellwangen; Konrad Holl, Aalen-Dewangen; Joachim Helmke; Hans-Joachim Kohnke, both of Kassel; August Winsel, Kelkheim, all of (DE)

(73) Assignee: Varta Geratebatterie GmbH (DE)

( * ) Notice: Subject to any disclaimer, the term of this patent is extended or adjusted under 35 U.S.C. 154(b) by 0 days.

(21) Appl. No.: 09/425,677

(22) Filed: Oct. 12, 1999

(30) Foreign Application Priority Data

Oct. 16, 1998 (DE) .......................... 198 47 706

(51) Int. Cl.⁷ ............................ G01N 27/404
(52) U.S. Cl. .............. 204/415; 204/432; 205/780.5; 205/781; 205/783
(58) Field of Search ............... 204/415, 431, 204/432

(56) References Cited

U.S. PATENT DOCUMENTS

| | | | |
|---|---|---|---|
| 2,898,282 A | * | 8/1959 | Flook et al. |
| 3,296,113 A | * | 1/1967 | Hansen |
| 3,455,807 A | * | 7/1969 | Jacobson et al. |
| 4,315,753 A | * | 2/1982 | Bruckenstein et al. |
| RE31,914 E | * | 6/1985 | Oswin et al. |
| 4,587,003 A | * | 5/1986 | Tantram et al. |
| 4,681,673 A | * | 7/1987 | Niedrach et al. |
| 5,298,146 A | * | 3/1994 | Braden et al. |
| 5,932,079 A | * | 8/1999 | Haupt et al. |
| 6,099,707 A | * | 8/2000 | Dunigan et al. |

FOREIGN PATENT DOCUMENTS

DE   1190 698   * 4/1965

OTHER PUBLICATIONS

Ives et al, "Reference Electrodes", (1961), pp. 71–72.*

* cited by examiner

Primary Examiner—T. Tung
(74) Attorney, Agent, or Firm—Schnader Harrison Segal & Lewis LLP

(57) ABSTRACT

An electrochemical gas sensor has a first gas diffusion electrode for a first reaction gas, which is inactive with respect to a second reaction gas at least in a first potential window, and a second gas diffusion electrode for the second reaction gas, which is active with respect to the second reaction gas at least in a second potential window for measuring two different gases in gas mixtures in a casing. The two gas diffusion electrodes are electronically isolated from one another, but electrically connected electrolytically to a reversibly loadable electrode and have contacts for connecting external closing circuits for adjusting the cell currents. The gas mixture is fed to the gas diffusion electrodes in series or parallel. The casing containing the electrodes is, in particular, in the form of a button cell. The reversibly loadable electrode is a Cu/CuO, Zn/ZnO or hydrogen electrode. The gas diffusion electrodes have a porous structure based on carbon or have a porous silver structure.

14 Claims, 1 Drawing Sheet

ELECTROCHEMICAL GAS SENSOR

FIELD OF THE INVENTION

The invention relates to an electrochemical gas sensor in a closed casing with gas openings for measuring gases in gas mixtures.

BACKGROUND OF THE INVENTION

A variety of methods are known for measuring the concentration of individual gases in gas mixtures. For example, DE-B 1190698 discloses a method for the determination of hydrogen or oxygen in a gas mixture, in which the gas mixture is fed through the gas space of a gas diffusion electrode, and the electrode potential and electrode current are then measured to determine the concentration of the gas. By way of example, this document also indicates that several gases, such as hydrogen and oxygen, can be determined in tandem by using one diffusion electrode each for hydrogen and oxygen, by feeding the gas mixture first to the oxygen electrode which ignores hydrogen, and then to the hydrogen electrode.

The document Journal of Power Sources 34 (1991), pages 331–338, A. Winsel and C. Fischer, "New apparatus for the measurement of the selfdischarge of the nickel hydroxide electrode" discloses a method for determining oxygen content by means of a zinc-air cell.

WO 97/35186 also discloses a method and a device for determining oxygen concentration, in which a zinc-air cell is used as the measuring element.

OBJECTS

Thus, an object of the invention is to determine the concentration of two gas components in a gas mixture, and to provide a suitable gas sensor which is simple and compact in design and operates reliably.

SUMMARY OF THE INVENTION

In the invention, a single electrochemical cell is used for measuring two gas components in a gas flow. For example, oxygen and hydrogen or oxygen and nitrous oxide can be measured in a gas flow. The electrochemical gas sensor can, therefore, be employed in conjunction with an anesthetizing device, to measure oxygen concentrations and nitrous oxide concentrations, or may be used at the output of methanol reformers to measure nitrogen and oxygen content.

BRIEF DESCRIPTION OF THE DRAWING

The subject matter of the invention is explained in more detail below with reference to the figure in which:

The figure shows a schematic representation of an electrochemical measuring cell according to the invention.

DETAILED DESCRIPTION OF THE INVENTION

Figure 1:
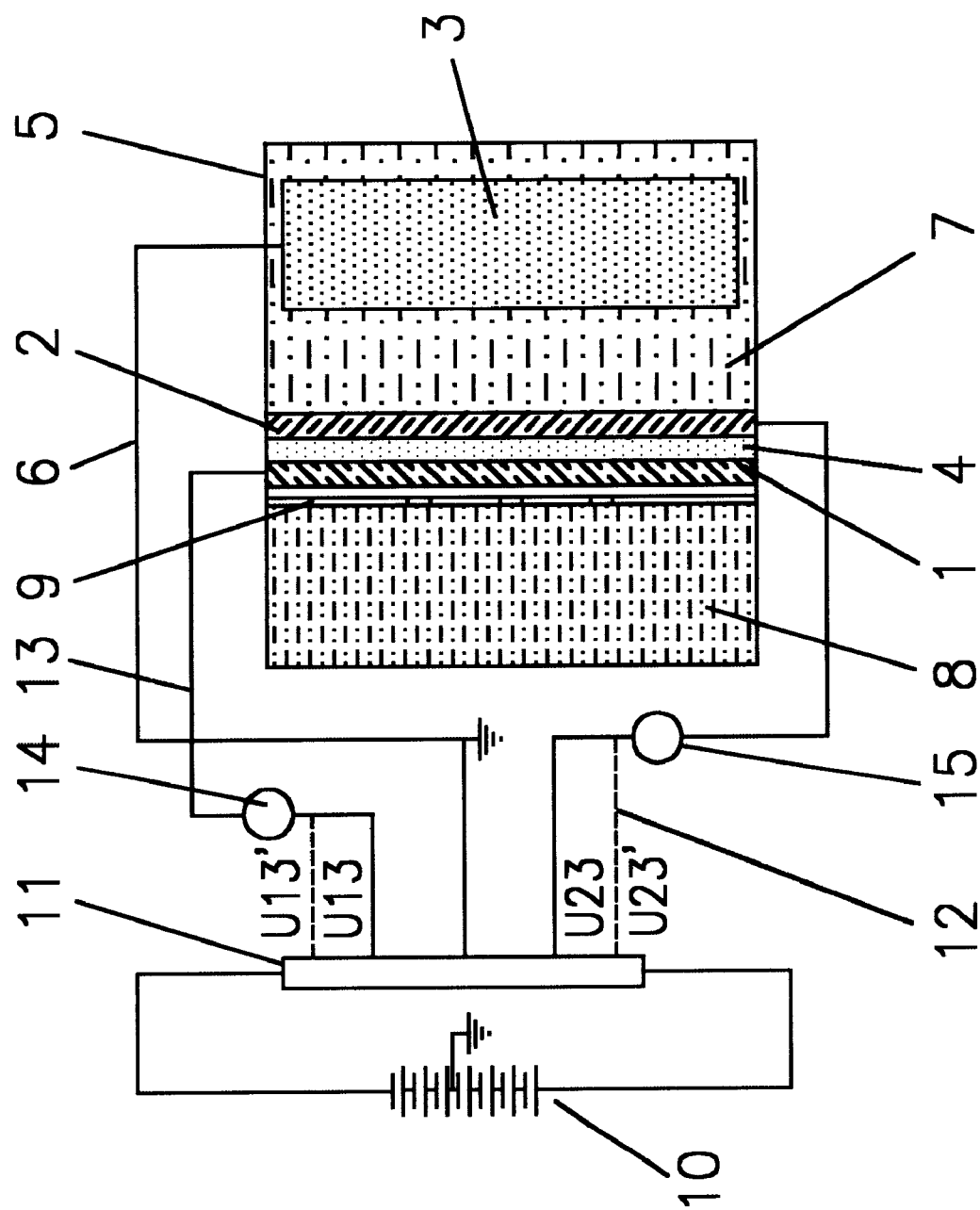

It will be appreciated that the following description is intended to refer to specific embodiments of the invention selected for illustration in the drawing and is not intended to define or limit the invention, other than in the appended claims.

Autothermic methanol reforming is often used for the hydrogen supply of fuel cells. In this case, a mixture of methanol, water and optionally oxygen is fed to a reformer which produces from this a gas mixture made up of hydrogen, carbon dioxide, carbon monoxide and steam for the fuel cells. In this atmosphere, conventional gas sensors do not selectively register oxygen with the desired accuracy of a few ppm, and also do not accurately detect the two gases, oxygen and hydrogen, together. An evaluation cannot, therefore, generally be made as to whether too little oxygen is being supplied, and the autothermic process fails. Even excessive oxygen admixture can be registered only with difficulty in the output flow when using conventional sensors. According to the invention, simultaneous measurement of both gases is possible with the cell schematically represented in the figure.

The gas sensor according to the invention preferably has a closed or sealed cell casing 5 with an anodically and cathodically loadable copper/copper oxide electrode 3, electrolyte 7 and a combination of gas diffusion electrodes. This electrode combination consists of two elementary electrodes 1 and 2, electrically isolated from one another with separator 4 in the form of a biporous layer which has interpenetrating electrolyte and gas pore systems. On the side facing gas 8, the electrode combination is closed off by partition 9 which restricts diffusion and is made of an insulant.

The gas sensor according to the invention is connected to an electrical circuit with which it is possible to set two voltage windows. The circuit has a DC source 10, which is connected to a voltage divider 11. The center tab 6 of voltage divider 11 is connected to Cu/CuO electrode 3 of the sensor. Voltage tab 12, with a lower voltage, connects to the $H_2$ electrode 2 whose zero-current potential is denoted $U_{23}$. $U_{23}$–$U_{23'}$ is, therefore, the loading window for this electrode relative to the Cu/CuO electrode. Correspondingly, tab 13 with the higher voltage $U_{13}$ is the loading voltage of the oxygen electrode 1, whose working window is represented by $U_{13}$–$U_{13'}$. Ammeters 14 and 15 are provided for measuring current in both leads 12, 13.

The flow of gas from gas space 8 into the combination of the gas diffusion electrodes 1 and 2 is restricted by a perforated partition 9. If there is oxygen in the gas space, then it reaches the oxygen electrode 1 by diffusion or flow and is reduced at that location. Its concentration is read as a current from measuring instrument/ammeter 14. For this purpose, the voltage window needs to be adjusted in such a way that the oxygen electrode 1 operates in the limiting current range. The oxygen then behaves as an inert gas which is entrained by the remaining gas mixture, which reaches the hydrogen electrode 2 adjusted to limiting current load and is electrochemically reduced at the potential of the electrode. The current then produced can then be read from measuring instrument/ammeter 15 and directly indicates the hydrogen content of the gas supplied. The separation layer 4 arranged between the two gas diffusion electrodes 1 and 2 must on the one hand electronically isolate, and on the other hand electrolytically conduct and sufficiently ensure flow and diffusion of the gas. These conditions can be achieved with known biporous structures of hydrophilic and hydrophobic powder mixtures, for example made up of polytetrafluoroethylene and aluminum oxide or ion-exchange resins.

The electrochemical measuring cell according to the invention, represented in the figure, therefore, has a reversibly loadable electrode 3 with high capacity, a first gas diffusion electrode 1 with high capacity for the first reaction gas (oxygen cathode), which is inactive with respect to the second reaction gas at least in a first potential window, and a second gas diffusion electrode 2 with high capacity for the second reaction gas (hydrogen anode), which is active with respect to the second reaction gas at least in a second potential window. The first and second gas diffusion electrodes are arranged in such a way that the second gas diffusion electrode receives the reaction gas via the first gas diffusion electrode. The gas diffusion electrodes are electrically isolated from one another and are electrolytically connected to one another via their electrolyte-filled pore systems and a separator and to the reversibly loadable electrode 3.

The measurement of hydrogen, besides oxygen and nitrogen, takes place with a three-electrode cell according to the invention by using a porous oxygen electrode structure without catalytic additives for the chemisorptive cleavage of hydrogen as the first gas diffusion electrode 1. In contrast, second gas diffusion electrode 2 is used with catalytic additives, such as platinum, palladium and nickel. The potential of electrode 1 is adjusted into the cathodic oxygen consumption window so that the oxygen entering through partition 9 is reduced without leaving a residue. Its content can be read from ammeter 14. The gas in hydrophobic/hydrophilic layer 4, therefore, still contains only nitrogen and hydrogen. The gas diffusion electrode 2 is adjusted into the potential window of the anodic hydrogen limiting current. The hydrogen is, therefore, consumed without leaving a residue in gas diffusion electrode 2. Ammeter 15, therefore, indicates the hydrogen content of the gas. The reversible electrode 3 is the reference electrode both for the oxygen cathode and for the hydrogen anode. It can fulfill this function so long as it is not in the fully reduced or fully oxidized state. Should this occur, it can be returned to a functional state by loading relative to one of the other two electrodes.

Another application area for a three-electrode cell according to the invention is the determination of oxygen and nitrous oxide ($N_2O$) in air for breathing. Instead of the Cu/CuO electrode, a zinc electrode of the type used in conventional primary cell technology is expediently used in this case. A zinc electrode with a conductive copper skeleton according to DE-A 4333291 is also suitable. The first gas diffusion electrode 1 is an oxygen cathode without hydrogen catalyst and without silver, which is set in a window>about+ 0.8V relative to the zinc electrode. The second gas diffusion electrode 2 is a porous silver structure, which is set in a window<about+0.8V relative to the zinc electrode. Under these circumstances, the nitrous oxide contained in the gas flow is inert at gas diffusion electrode 1, while it is reduced at gas diffusion electrode 2. The current in ammeter (measuring instrument) 14, therefore, indicates the oxygen content of the breathing gas, and the current in ammeter (measuring instrument) 15 the nitrous oxide content.

Input voltages $U_{12}$ and $U_{13}$ may be externally applied individual voltages, and the voltage window may in this case be formed by diodes and/or Zener diodes arranged in the circuit. The ammeters may be replaced by impedances, in particular, resistors across which a voltage drop corresponding to the amount of gas is measured. The three-electrode sensor cell, therefore, has a similar structure to a triode.

The gas sensor according to the invention may be incorporated in a modified button cell. This cell consists of a cylindrical casing part, in which middle reversible electrode is arranged as a common reference cathode and reference anode. Electrode may be an accumulative electrode, which must not react with $H_2$ or with $O_2$, or, alternatively, a reversible hydrogen electrode which is supplied with gas via supply tube. A separator, which has maximal barrier action for gases, is arranged on both sides of middle reversible electrode. Ionic exchange membranes are particularly suitable. On each side, middle reversible electrode is allocated a gas diffusion electrode, and respectively, which are respectively located in the metallic halves. Between the middle of case part the halves ring seals which provide sealing and electrical insulation of the parts are arranged.

Gas diffusion electrodes are configured in flow terms in such a way that the gas outlet is fed to an electrode at an inlet, flows through its gas space and exits at an outlet. This gas is subsequently fed into the gas space of the electrode at the inlet. From this electrode, gas is discharged to the atmosphere with maximally constant flow rate via a connection by an adjustable valve. In the case of measuring oxygen and nitrous oxide in a mixed gas, an oxygen cathode, of in particular, active carbon powder without other catalysts is used for the gas diffusion electrode. For the gas diffusion electrode, a porous silver structure or a silver-catalyzed active carbon is used. In this case, the electrode is capable of reducing only oxygen, but not the incoming nitrous oxide, although the gas diffusion electrode does have this capability. The measuring cell is supplied with the gas mixture via the inlet, the gas flow is fed firstly to gas diffusion electrode and then to gas diffusion electrode, and enters the atmosphere as waste gas via valve. If gas diffusion electrodes are operated in the voltage window for cathodic oxygen reduction in the limiting current range, the currents can be measured between middle electrode and gas diffusion electrode and gas diffusion electrode, respectively. The current between middle electrode and gas diffusion electrode corresponds to the oxygen concentration, and the current between middle electrode and gas diffusion electrode corresponds to the nitrous oxide concentration.

Gas is supplied to the electrochemical gas sensor via inlet, and is fed to gas diffusion electrodes via lines, it being possible to adjust the throughput to equal values by valves arranged at the outlets. In this arrangement, for example, oxygen in addition to hydrogen can be measured in a mixed gas. For this purpose, similar oxygen cathodes are used for gas diffusion electrodes, although the gas diffusion electrode is additionally catalyzed with platinum. Electrode 1 can only reduce oxygen, but not oxidize hydrogen. The electrode is, however, capable of oxidizing hydrogen. The measuring cell is supplied with the gas mixture via the inlet and the gas flow is apportioned in parallel to gas diffusion electrodes via the lines. If the gas diffusion electrodes are firstly operated in parallel in the voltage window for cathodic oxygen reduction with hydrogen-free gas, the two currents between the reversible electrode and the electrodes, respectively, can be adjusted to the same value with the aid of the valves. If hydrogen is added to the mixed gas, then it is inert in the electrode. For equal oxygen partial pressure, the current between the reversible electrode and the diffusion electrode thus remains constant. In the other electrode, however, the hydrogen is in addition anodically combusted, and the current delivered by the oxygen is, therefore, decreased by twice the amount of the anodic hydrogen oxidation. Using the voltage drop between the electrodes and the voltage drop between the electrodes, the gas concentrations can be determined by calculation, or read after calibration.

With the three-electrode cell, the measuring method can be referred to as a differential method. In this case, the two outer gas electrodes are substantially identical in terms of their response to oxygen, but a hydrogen catalyst is only applied to the other electrode. The same gas flows past both with the same flow rate, and both are adjusted to the same load voltage with respect to the middle electrode.

The adjustment of the load voltage is carried out as an electrical short circuit through equal impedances $Z_1$ and $Z_2$, since in short circuit with the (powerful) hydrogen electrode the (sparsely supplied) oxygen cathodes are sure to be in the limit current range. In the $H_2$-free state, both electrodes deliver substantially equal currents $I_1$ and $I_2$, and, therefore, the same voltage drops across the impedances or resistors $Z_1$ and $Z_2$. The voltage $U_{12}$ is, therefore, virtually equal to zero. If there is hydrogen in the gas to be measured, then the cathodic current $I_2$ in the other electrode becomes smaller by the current corresponding to the consumption by the anodic oxidation of the hydrogen, and in the electrode it remains unchanged. The voltage drop across $Z_2$ is, therefore, decreased. The voltage $U_{12}$ is a measure of the hydrogen concentration of the gas to be measured, since the electrode catalyzed with nickel or platinum delivers a measuring current decreased by twice the amount of the anodic hydrogen current. The reason for this is that the electrochemical action is the same as if hydrogen and oxygen were reacting purely catalytically, that is to say without current. Such a measuring method is advantageous, in particular, when the monitoring of an otherwise hydrogen free gas is involved.

In the case of monitoring a patient's breathing air for nitrous oxide, the three-electrode cell is modified as follows: the electrode is an oxygen electrode insensitive to nitrous oxide. Nitrogen and nitrous oxide behave as inert gases with respect to the electrode. The other electrode contains or consists of silver. In the region of the hydrogen potential, it can thereby cathodically reduce nitrous oxide as well as oxygen. When a hydrogen electrode is used as the middle electrode, the three-electrode cell is here again an active DC source in both current branches. It produces its direct current by its own action. If it is desired to use another middle electrode which operates reversibly, then, through inserting a current source Q in the current path of the middle electrode, the working window can be adjusted effectively by making the impedances $Z_1$ and $Z_2$ from combinations of resistors, Zener and/or rectifier diodes.

In each case, the individual currents and, therefore, the gas flows in the individual electrodes can be ascertained simply from the voltages across the resistors $R_1$ and $R_2$. For example $U_{13}=R_1*I_1$. $I_1$ is the current of electrode 1 corresponding to the oxygen content in the gas to be measured. $U_{12}=R_1*I_1-R_2*I_2=R_1*(I_1-I_2)$ is a measure of the nitrous oxide in the gas to be measured. $U_{13}/U_{12}$ is, therefore, the relative proportion of the nitrous oxide in the oxygen.

$U_{12}$ is a differential signal and, therefore, represents the discrepancy between electrodes. As a null method, this method is highly sensitive and especially good for process control. It is also possible to divide the DC voltage source Q in two portions $Q_1$ and $Q_2$, one voltage source lying in each connection between the middle electrode and the gas electrode. This also allows an asymmetric configuration of the voltage windows for the electrodes.

The three-electrode cell explained in the figure can also be produced in the form of a button cell. This button cell consists of a lid and a cup. The lid contains reversible electrode with a separator. There is also an electrode insert, formed for example by first gas diffusion electrode which is in contact with the cup and which is electrolytically connected to the second gas diffusion electrode via hydrophobic/hydrophilic separator layer. Contact is made with this gas diffusion electrode via contact pin which is insulated and fed through electrode cup. The numeral denotes a feed-through seal for contact. Optionally, it is also possible for the electrode to be connected to the cell cup, while the electrode has an insulated feed through the cell cup. Besides this, a vent hole for admitting the reaction gas into the cell is provided. A ring seal is used to isolate and seal the casing parts.

In the sensor cells according to the invention, the oxygen electrode generally consists of a porous active carbon layer which is applied to a substrate and rendered hydrophobic by PTFE. The hydrogen electrode is constructed in substantially the same way, but additionally contains a catalyst, especially a noble metal catalyst, for example, from group VIII such as platinum, palladium, nickel and the like. In the case of measuring nitrous oxide, use may be made of a gas diffusion electrode which, besides active carbon and polytetraethylene, contains silver as a catalyst or which is designed as a porous silver electrode. The reversibly loadable electrode may be a Cu/CuO or zinc electrode, but it is also possible to use a reversibly operating hydrogen electrode, known per se, for example a double-skeleton valve electrode (see E, Justin and A. Winsel in "Brennstoffzellen—Fuel Cells", Steiner-Verlag, Wiesbaden (1962), pages 67 et seq.).

If required by the design configuration of the sensor cell, the gas diffusion electrodes may be divided off from the gas openings by hydrophobic membranes to prevent electrolyte from escaping.

Although this invention has been described in connection with specific forms thereof, it will be appreciated that a wide variety of equivalents may be substituted for the specific elements described herein without departing from the spirit and scope of the invention as described in the appended claims.

We claim:

1. An electrochemical gas sensor for measuring a first and a second reaction gas in a gas mixture, said gas sensor comprising:
   a substantially sealed casing having gas openings and a gas space;
   a first gas diffusion electrode for said first reaction gas which is inactive with respect to a second reaction gas at least in a first potential window;
   a second gas diffusion electrode for said second reaction gas which is active with respect to the second reaction gas at least in a second potential window;
   a separator for electrically isolating said first and second gas diffusion electrodes from one another, said separator comprising a bi-porous layer having an interpenetrating electrolyte system and gas pore system;
   anodically and cathodically reversibly loadable electrode electrolytically connected to said first and second diffusion electrode by an electrolyte; and
   a hydrophobic membrane capable of passing said gas mixture to each of said electrodes and preventing said electrolyte from entering said gas space; and
   electrical contacts on each of said electrodes for connecting to external measurement circuits for determining and adjusting the current flow among said reversible electrode and said first and second gas diffusion electrodes.

2. The electrochemical gas sensor as claimed in claim 1, wherein said gas diffusion electrodes are adapted to contact said gas mixture in series.

3. The electrochemical gas sensor as claimed in claim 1, wherein said gas diffusion electrodes are adapted to contact said gas mixture in parallel.

4. The electrochemical gas sensor as claimed in claim 1, wherein said casing containing said electrodes is in the shape of a button cell.

5. The electrochemical gas sensor as claimed in claim 1, wherein said reversibly loadable electrode is a middle electrode and arranged between said gas diffusion electrodes.

6. The electrochemical gas sensor as claimed in claim 1, wherein said reversibly loadable electrode is a Cu/CuO, Zn/ZnO or hydrogen electrode.

7. The electrochemical gas sensor as claimed in claim 1, wherein at least one of said gas diffusion electrodes has a porous structure based on carbon.

8. The electrochemical gas sensor as claimed in claim 1, wherein at least one of said gas diffusion electrodes has a porous structure based on carbon with a noble metal catalyst.

9. The electrochemical gas sensor as claimed in claim 1, wherein at least one of said gas diffusion electrodes has a porous structure based on carbon with a silver catalyst.

10. The electrochemical gas sensor as claimed in claim 1, wherein at least one of said gas diffusion electrodes has a porous silver structure.

11. The electrochemical gas sensor as claimed in claim 1 further comprising an ammeter connected to each of said contacts to measure current generated from said gas diffusion electrodes.

12. The electrochemical gas sensor of claim 11 further comprising an electrical circuit including a DC source and a voltage divider connected to said ammeters.

13. The electrochemical gas sensor of claim 1, wherein said gases are hydrogen and oxygen.

14. The electrochemical gas sensor as claimed in claim 1, wherein said reversibly loadable electrode connects to said voltage divider.

* * * * *